(12) United States Patent
Fabian et al.

(10) Patent No.: US 7,307,530 B2
(45) Date of Patent: Dec. 11, 2007

(54) SURGICAL IMPLEMENT DETECTOR UTILIZING A RADIO-FREQUENCY IDENTIFICATION MARKER

(76) Inventors: Carl E. Fabian, 5001 London Walk, Miami, FL (US) 33138; Dave Narasimhan, 6 Summit Trail, Flemington, NJ (US) 08822

( * ) Notice: Subject to any disclaimer, the term of this patent is extended or adjusted under 35 U.S.C. 154(b) by 175 days.

(21) Appl. No.: 11/055,348

(22) Filed: Feb. 10, 2005

(65) Prior Publication Data

US 2006/0187059 A1   Aug. 24, 2006

(51) Int. Cl.
*G08B 13/14* (2006.01)

(52) U.S. Cl. ............... 340/572.1; 340/571; 340/572.4; 340/572.8

(58) Field of Classification Search ............ None
See application file for complete search history.

(56) References Cited

U.S. PATENT DOCUMENTS

| | | | |
|---|---|---|---|
| 4,114,601 A | 9/1978 | Abels | 128/1 |
| 4,193,405 A | 3/1980 | Abels | 128/296 |
| 4,658,818 A | 4/1987 | Miller, Jr. et al. | 128/303 |
| 5,057,095 A * | 10/1991 | Fabian | 604/362 |
| 5,153,583 A * | 10/1992 | Murdoch | 340/10.34 |
| 5,188,126 A | 2/1993 | Fabian et al. | 128/899 |
| 5,190,059 A | 3/1993 | Fabian et al. | 128/899 |
| 5,329,944 A | 7/1994 | Fabian et al. | 128/899 |
| 5,345,231 A * | 9/1994 | Koo et al. | 340/870.31 |
| 5,541,604 A * | 7/1996 | Meier | 342/42 |
| 5,664,582 A | 9/1997 | Szymaitis | 128/898 |
| 5,931,824 A | 8/1999 | Stewart et al. | 604/358 |
| 6,026,818 A | 2/2000 | Blair et al. | 128/899 |
| 6,076,007 A | 6/2000 | England et al. | 600/424 |
| 6,239,737 B1 * | 5/2001 | Black | 342/51 |
| 6,366,206 B1 * | 4/2002 | Ishikawa et al. | 340/573.1 |
| 6,424,262 B2 | 7/2002 | Garber et al. | 340/572.3 |
| 6,486,783 B1 * | 11/2002 | Hausladen et al. | 340/572.8 |
| 6,624,753 B2 * | 9/2003 | Elston | 340/572.8 |
| 6,734,795 B2 * | 5/2004 | Price | 340/572.1 |
| 6,838,990 B2 | 1/2005 | Dimmer | 340/572.4 |
| 6,861,954 B2 * | 3/2005 | Levin | 340/572.1 |
| 7,019,650 B2 * | 3/2006 | Volpi et al. | 340/572.1 |
| 2002/0067263 A1 * | 6/2002 | Tafoya et al. | 340/572.1 |

(Continued)

FOREIGN PATENT DOCUMENTS

WO   WO/9830166   7/1998

*Primary Examiner*—Benjamin C. Lee
*Assistant Examiner*—Son Tang
(74) *Attorney, Agent, or Firm*—Ernest D. Buff & Associates, LLC; Ernest D. Buff; Gordon E. Fish (57) ABSTRACT

A radio-frequency surgical implement detection system detects surgical implements in a surgical wound during and at the completion of a surgical procedure. Surgical implements, including surgical sponges or laparotomy pads, gauze pads and metallic surgical instruments, are individually attached to a non battery-powered, encapsulated radio-frequency marker. The marker comprises an integrated chip having a burnt-in memory code, which is broadcast through an antenna using a modulated carrier frequency. The code is received by an interrogating antenna of a detector. The interrogating antenna provides a power pulse, which is received by the antenna of the radio-frequency marker. The power pulse charges a capacitor, which proves power for the read function, carrier frequency modulation function and broadcast function of the integrated chip, permitting each marker-containing implement to be specifically identified.

9 Claims, 6 Drawing Sheets

U.S. PATENT DOCUMENTS

| | | |
|---|---|---|
| 2002/0143320 A1 | 10/2002 | Levin ............................. 606/1 |
| 2003/0006762 A1* | 1/2003 | Clements .................... 324/239 |
| 2003/0006878 A1 | 1/2003 | Chung ....................... 340/5.25 |
| 2003/0057279 A1 | 3/2003 | Uozumi et al. ............. 235/451 |
| 2003/0066537 A1 | 4/2003 | Fabian et al. ............... 128/899 |
| 2003/0105394 A1 | 6/2003 | Fabian et al. ............... 600/407 |
| 2003/0192722 A1 | 10/2003 | Ballard .................... 177/25.19 |
| 2004/0129279 A1 | 7/2004 | Fabian et al. ............... 128/899 |
| 2004/0201479 A1 | 10/2004 | Garber et al. ............ 340/572.1 |
| 2004/0250819 A1 | 12/2004 | Blair et al. .................. 128/899 |
| 2005/0003757 A1 | 1/2005 | Anderson .................. 455/41.1 |
| 2005/0258542 A1* | 11/2005 | Fuller et al. ................. 257/759 |

* cited by examiner

SURGICAL IMPLEMENT DETECTOR UTILIZING A RADIO-FREQUENCY IDENTIFICATION MARKER

BACKGROUND OF THE INVENTION

1. Field of the Invention

The present invention relates to radio-frequency identification (RFID) markers for detection of surgical implements; and more particularly, to use of an RFID marker embedded in or otherwise securely attached to a surgical implement, such as a laparotomy pad or sponge, metallic surgical instrument, or other implement, for preventing the inadvertent retention of such implement during a surgical procedure.

2. Description of the Prior Art

Many patents disclose methods for detection of surgical implements following surgery prior to wound closure. Such detection methods incorporate x-ray opaque markers within surgical implements and effect detection using postoperative x-ray of the patient or of discarded sponges. Also disclosed as being suitable for detection of surgical implements are methods involving use of resonant tags made from magnetomechanical elements, capacitors, LRC oscillatory circuits and smart markers.

U.S. Pat. Nos. 4,114,601 and 4,193,405 to Abels disclose a medical and surgical implement detection system. Surgical implements such as metallic instruments, sponges, implantable devices and indwelling therapeutic devices and materials are detected within the human body or other area of interest by incorporating or adding a radio-frequency transponder. A microwave system mixes two fundamental microwaves having 4.5-5 GHZ frequencies and relies on a non-linear transponder to produce higher order product frequencies. The transponder may be a thin film of a ferrite material exhibiting gyro-magnetic resonance at selected frequencies or a solid-state device containing diodes and field effect transistors. A non-linear transponder signal is received by a receiving antenna and filtered to remove all fundamental microwave frequencies. Unfortunately, substantially all of the higher order microwave frequencies generated by the transponder are readily absorbed by the human body. Consequently, most higher order microwave frequency signals are lost before any non-linear transponder can be detected. In addition, the gyro-magnetic effect produces a relatively weak signal.

U.S. Pat. No. 4,658,818 to Miller, Jr., et al. discloses an apparatus for tagging and detecting surgical implements. A miniature battery-powered oscillator is attached to each surgical implement and activated prior to its initial use. The output of each oscillator has the form of a low powered pulse of 1-10 MHZ frequency, and is coupled to the body's fluids and tissue. Following surgery but prior to suturing, a detection system senses for any pulses generated by the oscillator within the body. The surgical implement detection system disclosed by the '818 patent is not passive. It requires a miniature battery, which is turned on at the beginning of the operation. When the operation is complete, the battery may have already discharged, in which event the surgical implement will not be detected by the apparatus.

U.S. Pat. No. 5,057,095 to Fabian discloses a surgical implement detector utilizing a resonant marker for use in human or animal tissue. The marker is triggered into resonance by the interrogating field. A resonance frequency signal emitted by the marker is detected by a separate detection circuit adjacent to the interrogating circuit. The marker resonates due to magnetostriction properties of an amorphous metal ribbon, a piezoelectric device or a tuned LRC circuit. The response from the marker constitutes a simple sine wave having a particular frequency, which is less than one gigahertz. A detector is responsive within an interrogation zone encompassing a surgical wound. The marker is adapted to undergo resonance solely at a preselected frequency below 1 GHz, causing a substantial change in its effective impedance. An electromagnetic dipole field is thereby generated, which produces an identifying signal identity. The interrogation means is also provided with a means for varying phase and/or direction of the interrogating field. A receiving means placed within the interrogation zone detects the "ring-down", phase-shift, impedance or other identifying characteristic of the element in resonance.

U.S. Pat. No. 5,188,126 to Fabian, et al. discloses a surgical implement detection system utilizing capacitive coupling for use in human or animal tissue. The system comprises a battery-powered marker, which is secured to the surgical implement and positioned within a surgical wound. A detection means has an antenna disposed in close proximity to the tissue. Means are provided for capacitance coupling of the marker with the antenna and activation of the battery-powered marker. A field generating means associated with the detection system generates an electromagnetic field having a predetermined frequency band ranging from about 10 MHz to 1 GHz. The electromagnetic field causes the marker to produce a signal in the form of a sinusoidal wave having unique signal identity. A battery powers the capacitive marker, which will not function when the battery is discharged. Inasmuch as there is no means to verify the status of the battery, this method for detection of surgical implements is vulnerable to battery failure.

U.S. Pat. No. 5,190,059 to Fabian, et al. discloses a surgical implement detector utilizing a powered marker for use in human or animal tissue. A battery-powered marker is secured to a surgical implement positioned within the wound. An electromagnetic field generating structure in the battery-powered marker is provided for generating within the transmitting zone an electromagnetic field having a predetermined frequency band, providing the marker with signal identity. The response from the battery-powered marker is a simple sine wave having a particular frequency. Such a response does not comprise a digital code; it lacks the capacity for identifying a surgical implement. Battery power is required; detection is not effected when the battery is discharged.

U.S. Pat. No. 5,329,944 to Fabian, et al. discloses a surgical implement detector having an acoustic marker appointed for use within animal or human tissue. The acoustic marker is battery powered and is retained in a watertight case. The marker produces an identifying acoustic signal with pre-determined frequency characteristics within the wound. The detector may be a stethoscope. The battery-powered acoustic marker runs constantly. When the battery runs down, the battery-powered acoustic marker stops emitting its characteristic acoustic frequency. This event may occur before all the surgical implements have been removed from the surgical wound, adversely affecting the marker's reliability.

U.S. Pat. No. 5,541,604 to Meier discloses transponders, interrogators, systems and methods for elimination of interrogator synchronization requirement. A Radio-frequency Identification (RFID) system has an interrogator and a transponder, the interrogator having a first tuned circuit of a powering frequency for sending a powering burst to a transponder, a filter/demodulator for receiving a wireless, modulated RF response from a transponder. The interrogator additionally has a second tuned circuit in electrical communication with a modulator. The second tuned circuit has a selected bandwidth about a communication frequency. The selected bandwidth does not substantially overlap the powering frequency and encompasses the bandwidth of the modulated carrier of the RF response. The carrier is modulated using pulse width modulation (PWM), pulse position modulation (PPM), frequency-shift keying modulation (FSK), or another type of modulation methods. The interrogator also has a controller in electrical communication with the filter/demodulator and the tuned circuits. It enables the first tuned circuit to send the powering burst during a first time period and enables the modulator in electrical communication with the second tuned circuit to receive the RF response during a second time period. The transponder has a tuned circuit. A tuning circuit in electrical communication with the tuned circuit modifies the frequency characteristics of the tuned circuit. The circuit is thereby tuned during the powering burst to the powering frequency. It is also tuned during the RF response to the communication frequency. The transponder also includes a demodulator in electrical communication with the tuned circuit for receiving the RF interrogation therefrom and for demodulating data from the RF interrogation. This current generation RFID device sends a preset code to the interrogator. It is powered entirely by the power burst signal provided in the first time period and is capable of transmitting the code at a high rate to the interrogator.

U.S. Pat. No. 5,664,582 to Szymaitis discloses a method for detecting, distinguishing and counting objects. A marker made from a nonmagnetostrictive strip of amorphous or crystalline material produces higher harmonic excitations when energized by an alternating magnetic field. The higher harmonics are detected by the exciting antenna. This passive, non battery-powered device receives a fixed second harmonic frequency sinusoidal signal based on the size, shape and material of the marker. Information is not digitally encoded and therefore the marker has no means for identifying individual counting objects.

U.S. Pat. No. 5,931,824 to Stewart, et al. discloses an identification and accountability system for surgical sponges and includes machine-readable information located on a plurality of surgical sponges used in the surgical procedure. At the end of an operation the surgical implements are machine read to determine whether any of the sponges are missing. The system also includes an x-ray detector for the detection of missing sponges. Detection of sponges placed within a surgical wound is not effected unless the absence of a sponge is detected during the sponge count procedure following surgery. Actual location of a missing sponge requires x-ray examination.

U.S. Pat. No. 6,026,818 to Blair, et al. discloses a tag and detection device. An inexpensive tag has the form of a ferrite bead with a coil and a capacitor, or a tag of flexible thread composed of a single loop wire and capacitor element. The detection device locates the tag by pulsed emission of a wide band transmission signal. The tag resonates with a radiated signal, in response to the wide band transmission. Resonation occurs at the tag's own single, non-predetermined frequency, within the wide band range. The pulsing action of the wide band transmission builds the non-predetermined, radiated signal intensity over the ambient noise levels. This radiated signal is a sinusoidal wave of non-predetermined frequency and does not have digital information that identifies a particular sponge or surgical pad.

U.S. Pat. No. 6,076,007 to England, et al. discloses surgical devices and their location. A surgical device, such as a catheter or a prosthesis, carries, at a predetermined location, a tag composed of a high permeability, low coercivity magnetic material having a magnetized bias element. The tag is interrogated with a rotating magnetic field. Interaction between the tag and the rotating magnetic field is detected by a flying null system to determine the location of the tag within the human or animal body. Typically, the marker will be in the form of a thin film, a wire or a strip. The response signal from the tag is a sinusoidal wave with no digital information. The detection system is based on flying null technology. The tag is used for locating a catheter tip, not a sponge or surgical pad within a surgical wound.

U.S. Pat. No. 6,424,262 and US Patent Application No. 20040201479 to Garber, et al. disclose applications for radio-frequency identification systems. An RFID target is used, together with magnetic security element and a bar code reader, to check out and manage library materials such as reference books, periodicals, and magnetic and optical media. This disclosure has nothing to do with detecting sponges or surgical pads in a surgical wound.

U.S. Pat. No. 6,838,990 to Dimmer discloses a system for an excitation leadless miniature marker. An excitation field excites a leadless marker assembly. The system comprises a source generator assembly having a power supply, an energy storage device, a switching network and an untuned source coil interconnected and configured to deliver a selected magnetic excitation signal waveform, such as continuous bipolar or unipolar waveform, or a pulsed magnetic excitation signal waveform. The power supply is configured to deliver power to energize the energy storage device. The switching network is configured to: direct electrical current through the source coil. It alternately switches between a first on position and a second on position. Stored energy is alternately transferred from the energy storage device to the source coil and from the source coil back to the energy storage device. The source coil is coupled to the switching network to generate an excitation signal. Untuned excitation is used by the source coil to look for resonance from a set of markers embedded in human tissue. Information is processed using an array sensor to three-dimensionally locate a given marker. This system does not locate sponges or surgical pads misplaced in a surgical cavity. The frequency response of a target is sinusoidal and has no digital capability.

US Patent Application No. 2002/0143320 to Levin discloses tracking medical products with integrated circuits. Radio-frequency identification devices comprising a microprocessor, memory, analog front end and antenna are used to communicate with a remote unit. The remote unit has a processor memory and transreceiver that receives digital data from radio-frequency identification devices attached to medical products, such as a pharmaceutical product, a blood product or a tissue product. The radio-frequency identification device is first scanned and then rescanned at the end of the surgical procedure. There is no indication that the radio-frequency identification devices are encapsulated. Neither is there any indication that the RFID devices are incorporated in a sponge, surgical pad or surgical implement. Further, there is no indication in the Levin application that the RFID devices are scanned during surgery to establish the location of the sponge or surgical pad. There is also no indication in Levin application that the RFID devices are scanned at the end of an operating procedure to establish that no sponges or surgical pads are left behind in a surgical cavity.

US Patent Application No. 2003/0006878 to Chung discloses a smart tag data encoding method. Information is stored in a smart tag having a memory. The smart tag has two memory portions. One of the partitions is permanent and cannot be erased. A second memory portion stores application specific data. The second memory portion also stores a relational check number, which validates the integrity of the data stored in the second memory, thereby detecting memory alteration or corruption. This smart tag data encoding method has nothing to do with detecting a sponge or surgical pad left behind in a surgical wound.

US Patent Application No. 2003/0057279 to Uozumi et al. discloses an identifying system for an overlapped tag. An RFID and one or more resonance capacitors connected through on-off switches may be turned on or off by a remote control circuit. The overlapping tags may be interrogated using an RFID system, or one or more resonance capacitors. The Uozumi et al. system does not detect sponges and surgical pads in a surgical wound, since they are not expected to overlap. Signals from the resonant capacitors of Uozumi et al. form a sine wave comprising electromagnetic radiation and do not carry a digital code US Patent Application No. 20030066537 to Fabian, et al. discloses a surgical implement detection system. Surgical implements used during an operating procedure are detected in human tissue. Markers attached to the surgical implements change their impedance at a preselected frequency in the presence of an electromagnetic field. The system uses a magnetomechanical element which vibrates at a preselected frequency when excited. This preselected frequency, when detected, indicates the presence of a surgical implement to which the magnetomechanical marker element is attached. The marker resonates only at a fixed frequency and provides no digital information suited for identifying a sponge or a surgical pad.

US Patent Application No. 20030105394 to Fabian, et al. discloses a portable surgical implement detector. Surgical implements used during an operating procedure are detected in human or animal tissue. Markers attached to the surgical implements change their impedance at a preselected frequency in the presence of an electromagnetic field. Each of the markers is thereby provided with signal-identifying characteristics. The portable detector sweeps the surgical cavity with a range of frequencies which excites and vibrates markers attached to surgical implements at preselected frequencies, causing their detection. The markers resonate at preselected frequencies in the form of sinusoidal waves, but do not provide digital data suited for identifying a sponge or surgical pad.

US Patent Application No. 20030192722 to Ballard discloses a system and method of tracking surgical sponges. The sponges have a radiopaque object embedded therein, which is visible when the sponge container is x-rayed. All sponges brought into the operating room are x-ray identified. A missing sponge is detected by this accounting process. The system does not actively detect whether a sponge is accidentally left behind in a surgical wound. The patient is not x-rayed to determine whether the missing sponge is inside the surgical wound.

US Patent Application No. 20040129279 to Fabian, et al. discloses a miniature magnetomechanical tag for detecting surgical sponges and implements. This tag is a magnetomechanical device and is excited by the interrogating magnetic field. The interrogating field is switched off, and the ring down characteristic of the resonant target is detected. The system does not provide digital means for identifying a sponge or surgical pad.

US Patent Application No. 20040250819 to Blair, et al discloses an apparatus and method for detecting objects using tags and a wideband detection device. An apparatus and method for the detection of objects in the work area, such as surgical sites, including a detection tag affixed to objects used during surgery, is disclosed. The apparatus and method feature interrogates with a transmitter emitting a pulsed wideband signal, prompting the tag element to provide a return signal, which is received and analyzed. The device features an antenna portion containing a single or a plural ring-shaped antenna. Also, the pulsed wideband interrogation signal may be pulsed-width modulated or voltage-modulated. The pulsed signals trigger a continuing response signal from the tag in its response frequency range, which increases in intensity to the point where it becomes differentiable from background noise and is detected within the wideband range by the signal detector as an indication of the presence of the tag. The tag is excited by a wide band pulsed interrogation signal, which builds up the output of the tag and can be detected over ambient electronic noise. The tag signal has a predetermined frequency in the form of a sinusoidal wave, and does not carry digital information suitable for identifying laparotomy pads or sponges retained within the wound cavity.

US Patent Application No. 2005/0003757 to Anderson discloses an electromagnetic tracking system and method having a single-coil transmitter. The system includes a single coil transmitter emitting a signal, a receiver receiving a signal from the single coil transmitter, and electronics for processing the signal received by the receiver. The electronics determine a position of the single coil transmitter. The transmitter may be a wireless or wired transmitter. The receiver may be a printed circuit board. The electronics determine position, orientation, and/or gain of the transmitter. The single coil transmitter is a powered device and may be wired or wireless. It is not a passive device that can be incorporated in a sponge or surgical pad due to the requirement for a reliable power source.

PCT Patent Application No. WO 98/30166 to Fabian et al. discloses a surgical implement detector utilizing a smart marker. The surgical implement is appointed for disposition within human or animal tissue and is made to be electronically identifiable by affixing thereto a smart marker, which is an unpowered integrated circuit with EEPROM memory carrying a code. When the smart marker is sufficiently close to the reader antenna, a voltage is generated within the marker antenna that charges the capacitor and powers the integrated circuit. A switch is opened and closed to transmit the stored code in the EEPROM memory, providing identification and recognition of a smart target attached to a surgical sponge. The marker antenna operates at a frequency of near 125 KHz. The frequency of information transfer to the reader is very slow, due to the switching on and off action. Moreover, the smart marker is not encapsulated, and is subject to damage by blood and other saline fluids.

There remains a need in the art for a highly reliable, non battery-powered, surgical implement detection marker that may be attached to laparotomy pads or sponges, metallic and other surgical implements. Also needed is a marker of the type described, which can withstand cleaning and sterilization procedures commonly employed, and resists exposure to body fluids such as blood or saline solutions. A non battery-powered surgical implement marker and corresponding detection device, is needed to provide a reliable indication of the location of foreign objects within a surgical wound during and at the completion of a surgical procedure prior to wound closure

SUMMARY OF THE INVENTION

The present invention provides a surgical implement detector comprising a radio-frequency identification marker and a detection unit. This surgical implement detection marker is non battery-powered. It is highly reliable in operation and detects surgical implements such as metallic instruments, laparotomy pads or sponges, gauze pad and other surgical implements to which the radio-frequency marker is attached. The radio-frequency marker has a small size and is encapsulated in glass or inert polymer to withstand cleaning and sterilization operations. It is not adversely affected by blood or saline solution present in a surgical wound. This small radio-frequency marker has an antenna which couples with the interrogating antenna of the detection unit. A power burst from the interrogating antenna charges a capacitor located within the radio-frequency marker. The charged capacitor then powers the logic and processing functions of an integrated chip, which reads a burned-in code present in the read-only memory thereof. A carrier frequency is used for communication between the radio-frequency marker and the interrogating antenna of the detector. This carrier frequency is modulated by the dio frequency marker using pulse width modulation (PWM), pulse position modulation (PPM), frequency-shift keying modulation (FSK), or another modulation method to represent and communicate the coded numeric value. The interrogating antenna receives the modulated electromagnetic carrier wave and decodes, detecting the code communicated by the radio-frequency marker. This numeric code represents a specific surgical implement, which may be a laparotomy pad or sponge, metallic instrument, gauze pad or other implement, and is kept track of remotely during and after a surgical procedure.

Generally stated, the invention involves the use of one or more radio-frequency identification markers embedded in or otherwise securely attached to a sponge or laparotomy pad. A radio-frequency identification marker may also be attached to a metallic surgical instrument using a non-metallic extension, so that the radio-frequency marker is displaced from the metallic object. The metallic surgical instrument may shield the electromagnetic communication between the radio-frequency marker and the interrogating antenna. Such displacement procedure enables the communication. These surgical sponges or laparotomy pads are employed in a wide variety of applications during surgery, including removal of blood from a surgical cavity, control of excessive bleeding within the surgical cavity, and the like. The surgical implements may be accidentally left behind in the surgical cavity at the completion of the surgical procedure, resulting in severe infection possibility as well as rejection complications. The present invention overcomes this problem through use of sponges or laparotomy pads, gauze pad or metallic instruments incorporated with a radio-frequency identification (RFID) marker. When thus equipped with the RFID marker, the sponge, laparotomy pad, gauze pad or metallic instrument with which it is associated, is readily located by a hand-held scanner or a stationary scanner mounted upon a rollaway cart. A receiving unit detects a radio-frequency signal emitted by the marker. The signal represents a particular code. It causes immediate identification and detection of any and all laparotomy pads or surgical sponges, metallic instruments, gauze pad or other implements extant within the surgical cavity before closure of the surgical incision. Advantageously, with the present invention, the retention of non-metallic, particularly porous objects that may likely cause infection and tissue reaction is virtually eliminated.

Preferably, the radio-frequency marker is incorporated permanently within a laparotomy pad or surgical sponge. It may also be attached to a metallic instrument with a non-metallic extension. This radio-frequency marker includes a miniature integrated electronic circuit connected to an antenna, which is typically a copper wire wound over a ferrite core. A capacitor circuit acts as a power source when charged by the electromagnetic radiation power burst emitted by an interrogating antenna of a detecting remote unit. The antenna of the radio-frequency marker first couples with the interrogating antenna of the detecting remote unit, which may be a hand-held scanner or a fixed scanner adjacent to the operating table. An incoming burst of electromagnetic radiation is used to charge the capacitor. Upon being charged, the capacitor provides power to the integrated circuit, which reads a digital code that is permanently burned in the memory of the integrated circuit, and synthesizes a broadcast signal which modulates the carrier signal using pulse width modulation, pulse position modulation or frequency shift keying modulation. Digital data of the code is transmitted to the hand-held or fixed remote detection unit using the same antenna. Since the digital code, representing a laparotomy pad or surgical sponge, metallic instrument, gauze pad or other implement, cannot be generated by a device other than the particular radio-frequency identification device implanted, there is no room for error. The radio-frequency identification marker is encased in a glass envelope so that the sponge or laparotomy pad or metallic instrument can be effectively laundered, sterilized and packaged for single time use or multiple use. This radio-frequency identification marker is thus a passive device with a read-only memory of burnt digital code. It does not rely on battery power.

RFID tags are commercially available and operate at frequencies ranging from 125 KHz to 2.45 GHz. The lower frequency tags (about 125 KHz) are moderately resistant to shielding, but have only limited radio-frequency functionality due to bandwidth constraints. Such tags are useful for single tag interrogation. Due to the lower operating frequency, the tags tend to be bulky and expensive. At higher frequencies, (typically 13.56 MHz, 915 MHz, and 2.45 GHz), the increased bandwidth available allows processing of multiple tags in the interrogation zone during a short period of time. The preferred frequency of operation for radio-frequency targets for surgical instrument detection is 13.56 MHz to 2.45 GHz. These targets are typically small and inexpensive. High frequency markers are susceptible to shielding by adjacent metallic objects. For this reason, metallic instruments are provided with a non-metallic attachment that displaces the radio-frequency marker from the shielding metallic surface. In a surgical cavity large metallic objects are generally not present.

A surgeon scans each of the implements comprising laparotomy pads or surgical sponges, metallic instruments, gauze pad or other implements that he plans to use during the operation, before they are introduced into the incision. During surgery, the surgical wound is scanned to determine the location of the surgical implements. The surgical wound is scanned after the completion of surgery, prior to closure, to determine whether any surgical implements have been left behind. Each surgical implement has its own code. Accordingly, such remote hand-held or fixed scanning systems are error-free. As an added benefit, those surgical implements employed during surgery may be tracked as medical waste without having to handle each waste item.

BRIEF DESCRIPTION OF THE DRAWINGS

The invention will be more fully understood and further advantages will become apparent when reference is had to the following detailed description of the preferred embodiments of the invention and the accompanying drawing, in which.

DETAILED DESCRIPTION OF THE INVENTION

This invention relates to a surgical implement detector utilizing a radio-frequency identification marker which is embedded in a surgical sponge or laparotomy pad and is detected by a remote hand-held scanner or a fixed scanner. The scanner may be used to locate the so marked laparotomy pads or surgical sponges any time during surgery. More specifically, it is used to determine whether any foreign objects are left behind in a surgical cavity prior to surgical wound closure. The radio-frequency identification marker is an integrated circuit with a burned-in digital code in a read-only memory. It is powered by a capacitor circuit that is connected to an antenna, which comprises a ferrite element wound with copper wire. When the radio-frequency identification marker is in the presence of electromagnetic radiation, the antenna couples with the interrogating electromagnetic radiation, charges the capacitor and powers the integrated circuit, which accesses the burned-in digital code. This digital code is transmitted to the detector using the same antenna. The passive, radio-frequency marker is battery free and has infinite life with extreme reliability. The radio-frequency identification marker is encapsulated in a glass envelope so that the identification device may be incorporated in a sponge or surgical pad without being affected by blood, moisture and the like. With this housing, the unit may be laundered and sterilized without degrading its electronic circuit.

Generally stated, the invention involves the use of one or more radio-frequency identification markers or transponders, embedded in or otherwise securely attached to a laparotomy pad or surgical sponge, metallic instrument, gauze pad, or other implement. These surgical sponges or laparotomy pads enjoy a wide variety of uses during a surgical procedure, including absorption of blood and control of excessive bleeding within the surgical cavity, maintenance of tissues within desired position in the surgical cavity and the like. A particularly troublesome problem attending use of surgical implements results after the surgical procedure is complete. There exist numerous occasions where, following completion of surgery, the inserted surgical sponges or laparotomy pads, gauze pads or other implements are inadvertently left behind in the surgical cavity. This event oftentimes results in infection and adverse tissue reaction. The present invention overcomes this problem through use of passive glass-encapsulated radio-frequency identification (RFID) marker that is embedded or otherwise associated with laparotomy pads or surgical sponges. When thus equipped, the RFID marker, and hence the laparotomy pad or surgical sponge with which it is associated, is readily located by a handheld scanner or a stationary scanner that is carried on a roll-away cart. A receiving unit detects a radio-frequency signal emitted by the marker representing the digital code burnt-in the read-only memory therein, causing immediate identification and detection of any and all sponges and laparotomy pads situated within the surgical cavity before closure of the surgical incision. The surgeon may preferably scan each laparotomy pad or surgical sponge prior to operation. The patient is then interrogated with a scanner to exactly identify the location of a surgical sponge or laparotomy pad during operation. Scanning of the patient may also be carried out to determine which of the surgical sponges or laparotomy pads is contained within the surgical cavity. Advantageously, with the present invention, the retention of non-metallic, particularly porous objects that would likely cause infection and adverse tissue reaction is virtually eliminated.

More specifically, a radio-frequency transponder is incorporated permanently within a surgical sponge or laparotomy pad. Its passive electronic circuit is encapsulated in a glass envelope, thereby protecting it against damage from blood, moisture, laundering operations or sterilization procedures. The transponder includes a miniature integrated electronic circuit. It has an antenna, which is a copper wire wound over a ferrite core and a capacitor circuit, which acts as a power source. The antenna first couples with the detecting remote unit, which may comprise a handheld scanner or a fixed scanner adjacent to the operating table. Incoming radiation is used to charge the capacitor. Upon being charged, the capacitor provides power to the integrated circuit, which reads a digital code that is permanently burned in the memory of the integrated surface and synthesizes a broadcast signal of the digital data to the handheld or fixed remote detection unit using the same antenna. Since the digital code representing a surgical sponge or laparotomy pad cannot be generated by a device other than the particular radio-frequency identification device implanted, there is no room for error. The radio-frequency identification marker is encased in a glass envelope so that the sponge or laparotomy pad can be effectively laundered, sterilized and packaged for single time use. This radio-frequency identification marker is a passive device with a read-only memory of burnt-in digital code. The passive device uses the detector interrogation signal to charge the capacitor power source, which powers the integrated circuit to synthesize and transmit its digital code-carrying signal to the detector, without relying on battery power.

A number of manufacturers produce these radio-frequency markers. Most notable of these manufacturers are Texas Instruments, Hughes Identification Devices, Destron-Fearing Corporation. Modern RFID tags also provide significant amounts of user accessible memory, sometimes in the form of read-only memory or write-once memory. The amount of memory provided can vary, and influences the size and cost of the integrated circuit portion of an RFID tag. Typically, between 128 bits and 512 bits of total memory can be provided economically. For example, an RFID tag available from Texas Instruments of Dallas, Tex., under the designation "Tag-it" provides 256 bits of user programmable memory in addition to 128 bits of memory reserved for items such as the unique tag serial number, version and manufacturing information, and the like. Similarly, an RFID tag available from Philips Semiconductors of Eindhoven, Netherlands, under the designation "I-Code" provides 384 bits of user memory along with an additional 128 bits reserved for the aforementioned types of information. They operate at frequencies ranging from 125 KHz to 2.45 GHz. The lower frequency tags (about 125 KHz) are moderately resistant to shielding, but have only limited radio-frequency functionality due to bandwidth constraints. In particular, systems based on these markers generally operate reliably only when a single tag is in the interrogation zone at a time. They also tend to be relatively bulky and expensive to manufacture. At higher frequencies, (typically 13.56 MHz, 915 MHz, and 2.45 GHz), the added bandwidth available has permitted the development of systems which can reliably process multiple tags in the interrogation zone in a short period of time. However, the high frequency markers are susceptible to shielding by adjacent metallic objects. In a surgical cavity large metallic objects are generally not present. Accordingly, high frequency radio-frequency markers are preferred, owing to their small size and reduced manufacturing cost.

Figure 1:
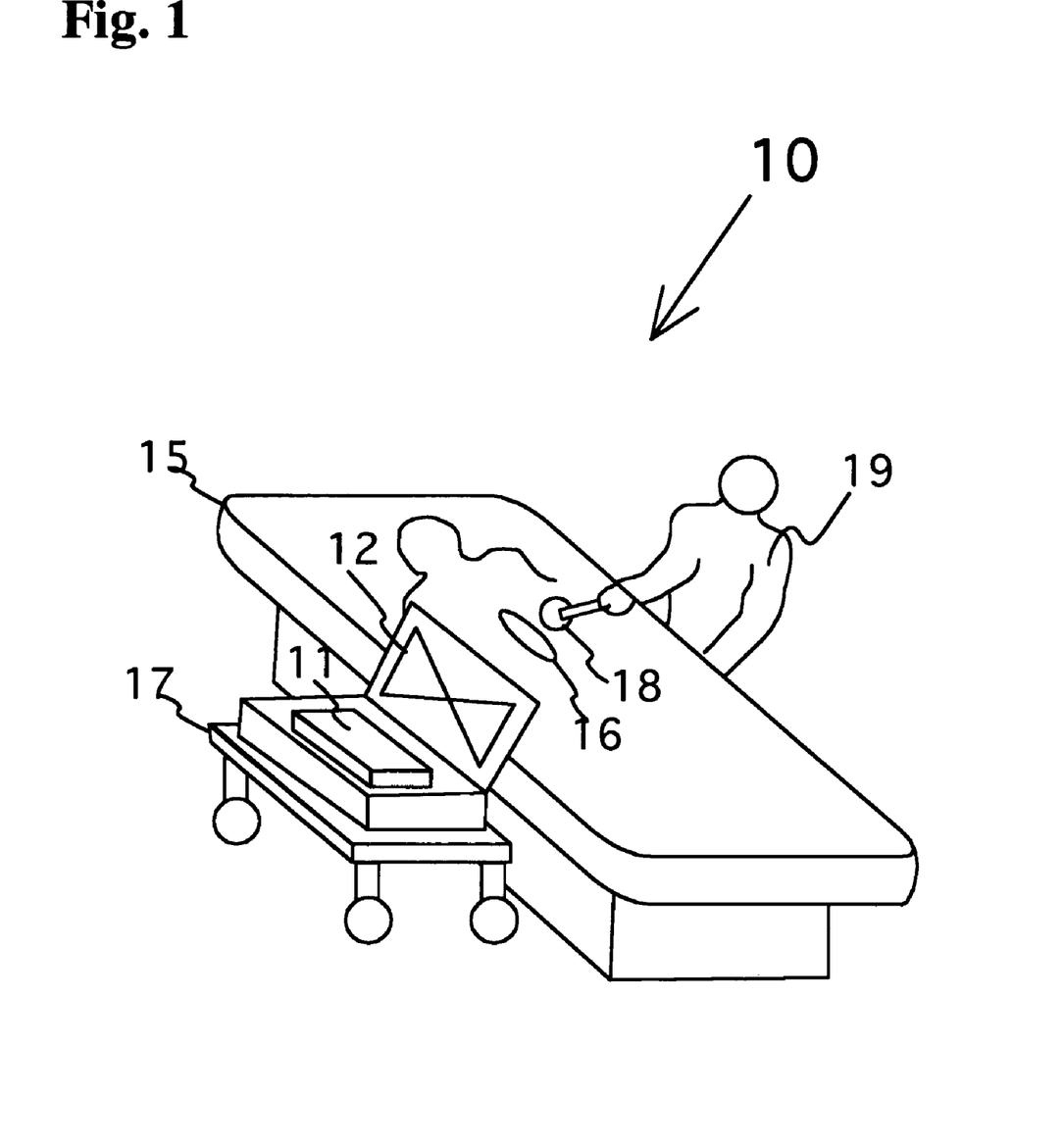
FIG. 1 is a schematic diagram showing a radio-frequency identification and detection system.

FIG. 1 is a schematic diagram showing a radio-frequency identification and detection system being utilized in an operating room 10. Detector 11 may be placed in close proximity to an operating table 15, which supports a patient having an incision 16. Detection system 11 may be conveniently mounted on a rolling cart 17 and brought close to the patient immediately after surgery and prior to closure of incision 16. Detector 11 has interrogating antenna 12 providing detection functionality for radio-frequency identification markers incorporated within surgical sponges or laparotomy pads. In an alternate embodiment, the detection system 11 can be incorporated into a handheld device 18, which is brought close to the patient by the doctor 19 for scanning in the vicinity of the surgical wound during and immediately after surgery and prior to wound closure. The detector 11 provides substantially error-free detection of marker tags attached to objects (including surgical sponges, gauze pads and the like) present within the surgical wound. A digital broadcast signal received by the detector provides an audible and/or visible warning when a specific sponge or laparotomy pad is present within the surgical incision.

Figure 2:
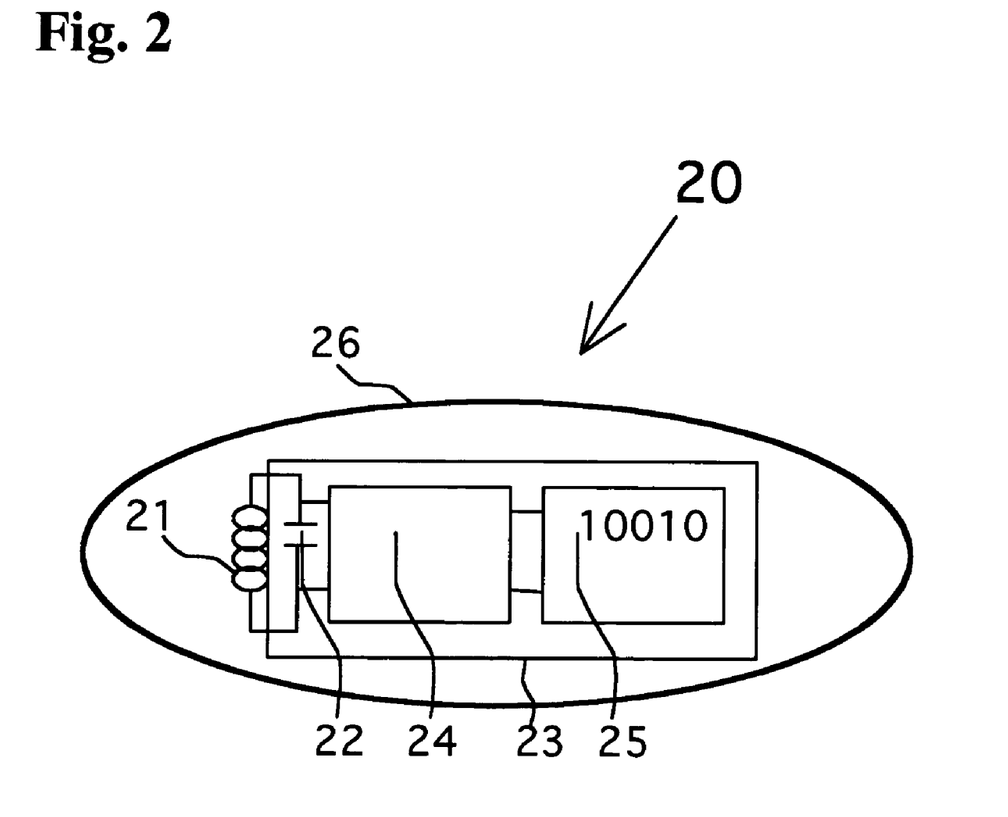
FIG. 2 is a diagrammatic representation of the details of construction of an encapsulated radio-frequency marker.

Referring to FIG. 2, there are shown generally at 20 the details of the radio-frequency marker. The marker has an antenna 21, which receives a power pulse from a remote detector-interrogating antenna (not shown) to charge a capacitor 22. This capacitor 22 becomes the power source for the operation of the non battery-powered radio-frequency marker, which has an integrated switch having an integrated circuit 23 which has a reading function, carrier-frequency modulating function 24 and a read-only memory portion 25 with a burnt-in code shown as '10010' in FIG. 2. The radio-frequency-integrated chip together with the antenna 21 is encapsulated in an enclosure resistant to blood, saline solution or water 26.

Figure 3:
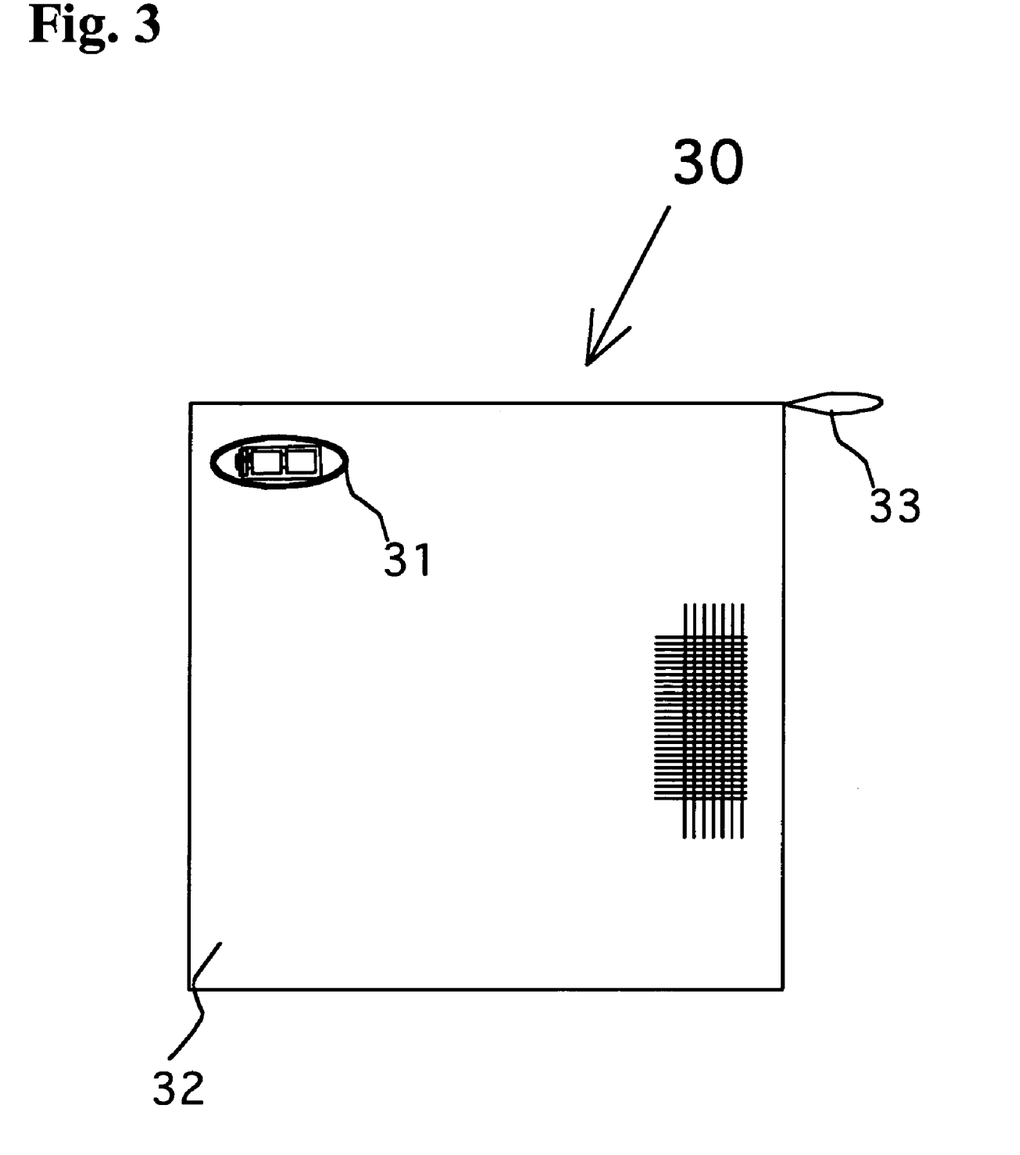
FIG. 3 is a diagrammatic representation of a sponge or laparotomy pad provided with a radio-frequency marker.

Referring to FIG. 3, there are shown generally at 30 certain details involving the incorporation of a radio-frequency marker in a surgical sponge (or laparotomy pad), which is typically fabricated from soft absorbent cloth, 14 or 18 inches square. The encapsulated radio-frequency marker 31 is incorporated inside a sponge 32. The surgical sponge or laparotomy pad typically has a fabric lanyard 33 sewn in or firmly attached to the pad.

Figure 4:
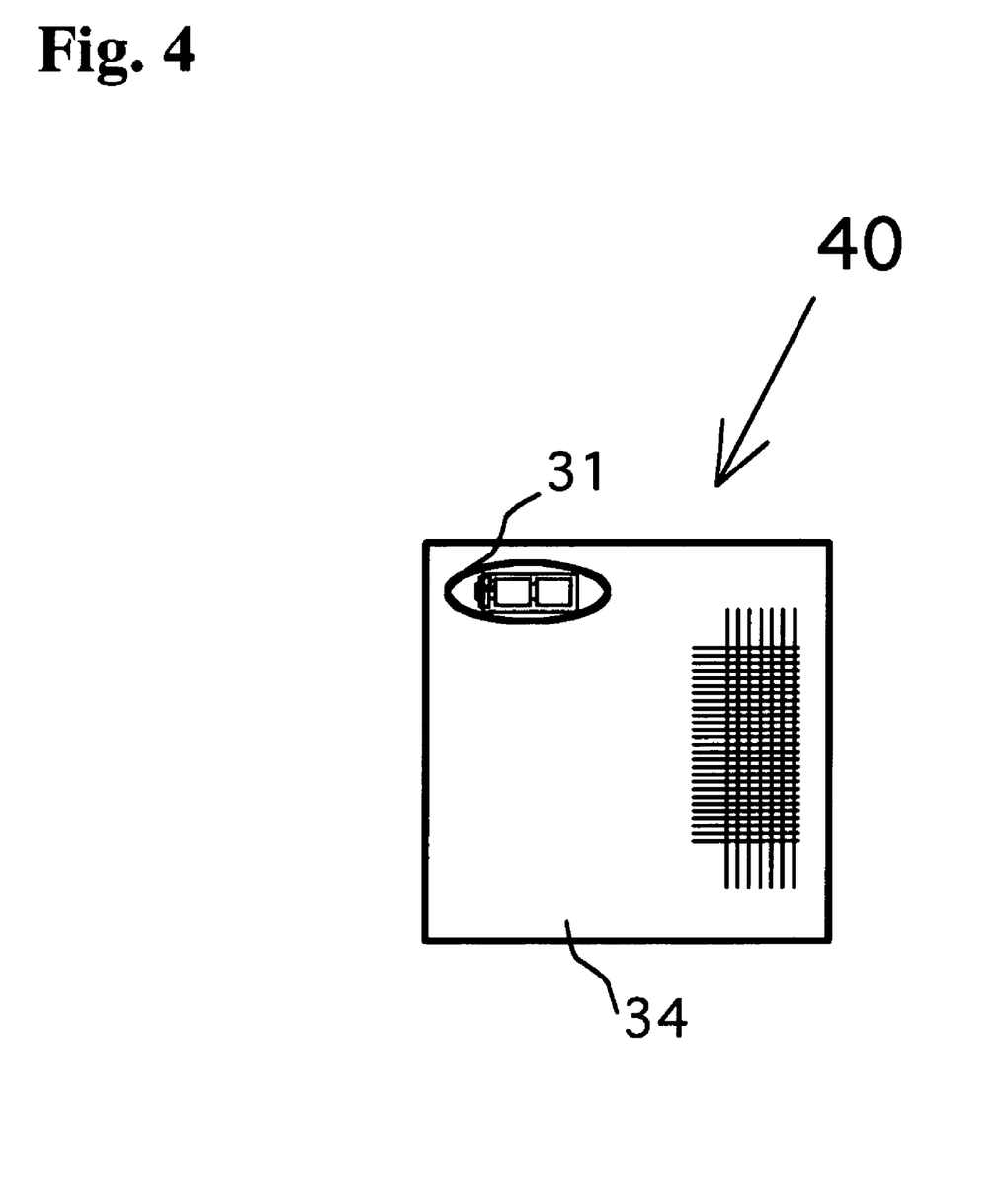
FIG. 4 is a diagrammatic representation of gauze pad provided with a radio-frequency marker.

Referring to FIG. 4, there are shown generally at 40 details involving the incorporation of a radio-frequency marker 31 into a gauze pad 34, which is typically a 4-inch square. The encapsulated radio-frequency marker 31 may be sewn into gauze pad 34 as shown.

Figure 5:
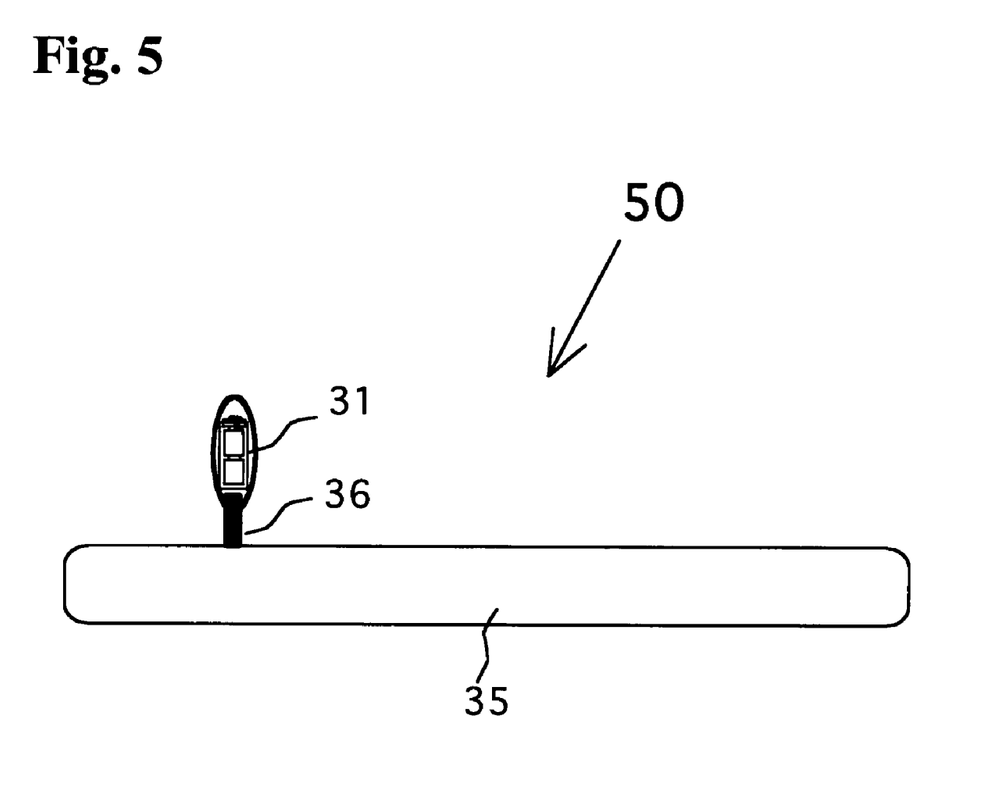
FIG. 5 is a diagrammatic representation of a metallic surgical retractor provided with a radio-frequency marker.

Referring to FIG. 5, there are shown generally at 50 details involving the incorporation of a radio-frequency marker 31 in a metallic surgical retractor 35. The metallic surgical retractor 35 has a non-metallic extender 36 which carries encapsulated radio-frequency marker 31 and displaces the marker from the metallic surface of the surgical instrument preventing any shielding effect.

Figure 6:
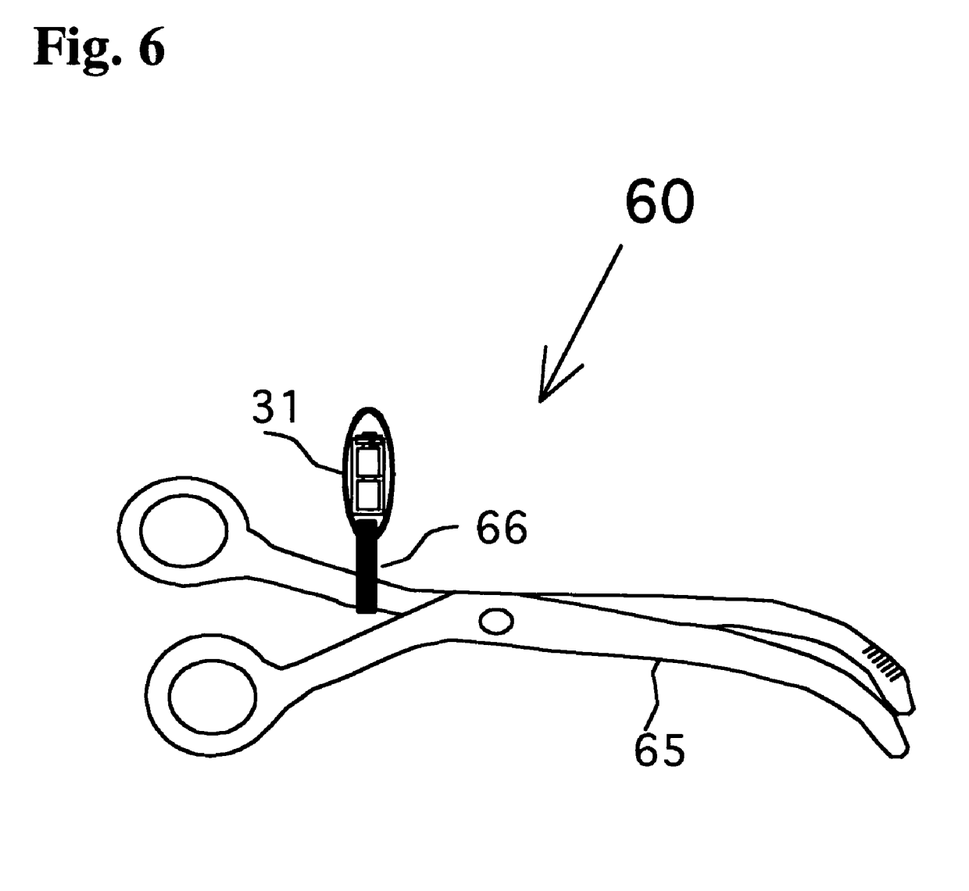
FIG. 6 is a diagrammatic representation of a metallic surgical clamp provided with a radio-frequency marker.

Referring to FIG. 6, there are shown generally at 60 details involving the incorporation of a radio-frequency marker 31 in a metallic surgical clamp 65. In order to prevent the shielding of the radio-frequency marker by the metallic surface of clamp 65, a non-metallic extender 66 is used to offset the encapsulated radio-frequency marker from the surgical clamp 65 as shown.

A smaller metallic surgical implement may only require a much smaller extender to prevent shielding effects.

Significant advantages are realized by practice of the present invention. The key components of the surgical implement detector utilizing radio-frequency identification marker includes, in combination, the features set forth below:

1. an integrated circuit, an antenna having wound copper wire on a ferrite core and a capacitor circuit;
2. the integrated circuit carrying a read-only digital code and being capable of synthesizing and broadcasting the digital code signal using the ferrite antenna when powered by the charged capacitor circuit;
3. the radio-frequency marker being encapsulated in a hermetically sealed glass envelope to withstand laundering, sterilization procedures and forces applied during packaging;
4. the encapsulated radio-frequency identification marker being permanently incorporated into surgical implements such as surgical sponges or laparotomy pads, metallic surgical instruments, or other implements used for surgery;
5. the surgical sponge or laparotomy pad, gauze pad, or metallic implement being interrogated prior to surgical incision closure by a handheld or fixed remote detector having an antenna that broadcasts a high frequency signal in the range of 125 KHz to 2.45 GHz, and preferably 13.56 MHz to 2.45 GHz;
6. the interrogation signal from the handheld or fixed remote detector charging the capacitor circuit of the radio-frequency marker, to provide power for operation of the integrated circuit, such operation including reading the digital code, synthesizing a PWM, PPM or FSK modulated broadcast carrier signal representing the digital code, and broadcasting the digital code signal through the antenna to the antenna coil of the detector;
7. the detector being operative to interpret the received digital code in the broadcast modulated carrier signal and match it with code created by previously scanned digital code data from surgical sponges or laparotomy pads or metallic surgical implements appointed for use during the surgical procedure;
8. detecting surgical sponges or laparotomy pads or metallic surgical implements retained within the surgical cavity; and, optionally,
9. using the handheld or fixed detector to identify and document as medical waste sponges and surgical pads previously utilized during the surgical procedure.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A surgical implement detector system, comprising:
   a. a non battery-powered, radio-frequency marker encapsulated in a glass envelope and attached to a surgical implement designated for use in a surface of a surgical procedure, said surgical implement being a metallic surgical instrument and said radio-frequency marker being displaced from said surface of said surgical instrument using a non-metallic fastener thereby preventing signal interfering effect from the metallic surgical implement;
   b. remote detector unit having an interrogating antenna that communicates with and powers the said radio-frequency marker using a carrier frequency;
   c. said radio-frequency marker comprising an integrated circuit comprising a read-only memory having a burnt-in code that is powered by a capacitor;
   d. said capacitor being charged by said interrogating antenna and coupling to a second antenna located within the radio-frequency marker to provide power thereto;
   e. said radio-frequency marker broadcasting said code through said radio-frequency antenna using a modulated carrier frequency, which is received by said interrogating antenna;
   f. said detector unit decoding said modulated carrier frequency and detecting said code, thereby identifying a surgical implement to which a radio-frequency marker is attached;
   whereby scanning a surgical wound using said remote detector interrogating antenna during and after an operating procedure detects the location and identity of surgical implements present within a surgical wound.

2. The surgical implement detector system as recited by claim 1, wherein said detector interrogating antenna operates at a carrier frequency of 13.56 MHz to 2.456 GHz.

3. The surgical implement detector system as recited by claim 1, wherein said remote detector is handheld.

4. The surgical implement detector system as recited by claim 1, wherein said remote detector is carried on a rollaway cart.

5. The surgical implement detector system as recited by claim 1, wherein said radio-frequency marker modulates said carrier frequency using pulse width modulation to broadcast said code.

6. The surgical implement detector system as recited by claim 1, wherein said radio-frequency marker modulates said carrier frequency using pulse position modulation to broadcast said code.

7. The surgical implement detector system as recited by claim 1, wherein said radio-frequency marker modulates said carrier frequency using frequency-shift keying modulation to broadcast said code.

8. A method of using a surgical detection system, comprising steps of:
   g. attaching a radio-frequency marker encapsulated in a glass envelope to a surface of a surgical implement selected for use in a surgical procedure, said surgical implement being a metallic surgical instrument and said radio-frequency marker being displaced from said surface of said surgical instrument using a non-metallic fastener thereby preventing signal interfering effect from the metallic surgical implement;
   h. scanning said surgical instrument with a remote detector interrogating antenna to identify its code and associate said code with a specific surgical instrument;
   i. scanning said surgical wound with said remote detector interrogating antenna during said surgical procedure;
   j. scanning said surgical wound with said remote detector interrogating antenna following completion of surgery but prior to wound closure to locate surgical instruments retained within said wound;
   k. determining the identity of said retained surgical instruments and removing them prior to wound closure.

9. A method of using a surgical detection system as recited by claim 8, further comprising the step of:
   1. scanning discarded surgical instruments to record disposal thereof as hazardous medical waste.

* * * * *